United States Patent [19]

Heiliger

[11] Patent Number: 5,534,630

[45] Date of Patent: Jul. 9, 1996

[54] BIOLOGICALLY ACTIVE INITIATORS FOR RADICAL POLYMERIZATION

[75] Inventor: Ludger Heiliger, Leverkusen, Germany

[73] Assignee: Bayer Aktiengesellschaft, Leverkusen, Germany

[21] Appl. No.: 320,597

[22] Filed: Oct. 7, 1994

Related U.S. Application Data

[63] Continuation of Ser. No. 130,880, Oct. 4, 1993, abandoned.

[30] Foreign Application Priority Data

Oct. 9, 1992 [DE] Germany ............................ 42 34 074.8
Jul. 9, 1993 [DE] Germany ............................ 43 22 885.2

[51] Int. Cl.$^6$ ............................. C08F 4/00; C07D 445/04
[52] U.S. Cl. ............................................ 534/752; 525/256
[58] Field of Search ............................... 534/752; 525/256

[56] References Cited

U.S. PATENT DOCUMENTS

| 3,117,961 | 1/1964 | Lange et al. ............................ 534/752 |
| 3,956,269 | 5/1976 | Sheppard et al. ........................ 534/682 |
| 4,155,937 | 5/1979 | Haas ........................................ 560/85 |

FOREIGN PATENT DOCUMENTS

| 0535458 | 4/1993 | European Pat. Off. . |
| 8601902 | 3/1986 | WIPO . |
| WO8901474 | 2/1989 | WIPO . |

*Primary Examiner*—Robert Gerstl
*Attorney, Agent, or Firm*—Connolly and Hutz

[57] ABSTRACT

Biologically active initiators (radical chain starters) have been discovered that have the general structure of formula (I)

$$A-L-B-[-L-A]_y \qquad (I),$$

wherein
  A signifies a biologically active part,
  B a radical-forming part,
  L a linker grouping and
  y the number 0 or 1, preferably 1.

Possible as the biologically active part A are for example biotin, digitoxin, digoxin, digitoxigenin, digoxigenin and oligonucleotides of 1 to 80, preferably 15 to 50 and in particular 20 to 35 nucleotide structural units.

4 Claims, No Drawings

BIOLOGICALLY ACTIVE INITIATORS FOR RADICAL POLYMERIZATION

This application is a continuation of application Ser. No. 08/130,880 filed on Oct. 4, 1993, now abandoned.

Biologically active initiators (radical chain starters) have been discovered that have the general structure of formula (I)

$$A-L-B-[-L-A]_y \qquad (I),$$

wherein

A signifies a biologically active part,

B a radical-forming part,

L a linker grouping and the number 0 or 1, preferably 1.

Suitable biologically active compounds which can be used as the biologically active part A are for example biotin, digitoxin, digoxin, digitoxigenin, digoxigenin and oligonucleotides of 1 to 80, preferably 15 to 50 and in particular 20 to 35 nucleotide structural units.

Biotin, digoxigenin and oligonucleotide of 15 to 50, in particular 20 to 35 nucleotide structural units are preferred.

The following groupings can, for example, be employed as the linker grouping L: —SO$_2$—, —COO—, —SO$_2$NH—, —CO—NH—, —NH—CO—O—, —NH—CS—O—, —NH—CO—NH—, —NH—CS—NH—, —O—, —NH—, —S—.

Preferred linker groupings are —CO—NH—, —NH—CO—NH—, —COO—, and —NH—CO—O— —CO—NH— and —NH—CO—NH— are particularly preferred.

The linker grouping L links together covalently the biologically active part and the radical-forming part B.

If an increased mobility of the structural units A and/or B is desired, a spacer function also can be exerted by L, in which case L can then consist of the following sub-units of formula (IV):

$$L^1-R-L^1 \qquad (IV),$$

wherein $L^1$ has the meanings indicated in connection with L and

R represents $C_1$-$C_{20}$ alkylene, preferably $C_3$-$C_{15}$ alkylene, particularly $C_5$-$C_{10}$ alkylene, $C_6$-$C_{10}$-arylene-$C_2$-$C_{10}$-alkylene, preferably phenylene- or naphthylene-$C_2$-$C_8$-alkylene, and $(CH_2-CH_2-O)_n$, wherein n signifies 1 to 20, preferably 3 to 15, and particularly 3 to 10.

The following compounds can be used as the radical-forming part B:

1) azo structures of the general formula (V):

$$R^{11}-N=N-R^{12} \qquad (V),$$

wherein $R^{11}$ and $R^{12}$ signify $C_1$-$C_{20}$ alkyl, $C_3$-$C_{10}$ cycloalkyl, $C_7$-$C_{20}$ aralkyl or the group

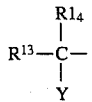

and

Y signifies CN, N$_3$ or

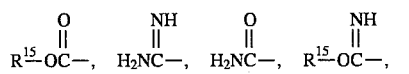

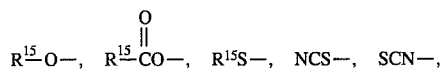

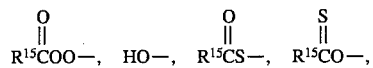

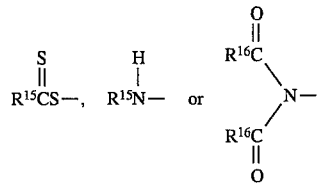

$R^{13}$, $R^{14}$ and $R^{15}$ independently of each other signify $C_1$-$C_{20}$ alkyl or $C_3$-$C_6$ cycloalkyl or, if $R^{13}$ and $R^{14}$ are linked, $C_2$-$C_{30}$ alkylene or additionally one of the groups $R^{13}$ or $R^{14}$, but not both simultaneously, signifies phenyl, tolyl, xylyl, benzyl or phenethyl, $R^{16}$ independently signifies $C_1$-$C_6$ alkyl, $C_3$-$C_6$ cycloalkyl or $C_6$-$C_{12}$ aryl;

2) tetraaryl/alkylethanes of the general formula (VI)

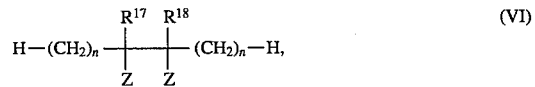

in which

Z represents hydroxy, $C_1$-$C_6$ alkyl or $C_6$-$C_{20}$ aryl, in particular hydroxy, methyl, ethyl, n- or isopropyl, phenyl or naphthyl, $R^{17}$ and $R^{18}$ independently of each other represent $C_1$-$C_6$ alkyl or $C_6$-$C_{20}$ naphthyl, in particular methyl, ethyl, n- or isopropyl, phenyl or naphthyl and n represents the numbers 1 to 6, preferably 1, 2, 3, 4 or 5;

3) dinitriles of formula (VII)

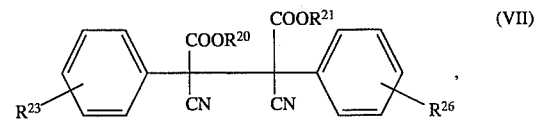

in which $R^{20}$, $R^{21}$ and $R^{23}$ independently of each other represent $(CH_2-)_m-H$, wherein m represents the numbers 1 to 6, preferably 1, 2, 3, 4 or 5;

4) peroxides of general formula (VIII)

in which l represents the numbers 0 to 6, preferably 0, 1, 2, 3 or 4, in particular 0, 1 or 2, and $R^{24}$ represents phenylene, naphthylene, $C_3$-$C_6$ alkylene or $C_3$-$C_6$ cycloalkylene.

The structures of the structural units B mentioned under 1) and 4) are preferred.

The compounds of formulae (V) to (VIII) are generally known (cf e.g. U.S. Pat. No. 3,956,269, Houben-Weyl, Makromolekulare Stoffe, Part 1, pages 16–19).

Preferred azo structures of formula (V) are compounds of formula (Va)

$$H \text{---} \left[ (CH_2)_p \text{---} \underset{\underset{Y^1}{|}}{\overset{\overset{R^{25}}{|}}{C}} \text{---} N = \right]_2 \quad \text{(Va)}$$

in which p signifies the numbers 1 to 20, preferably 1 to 15, in particular 2 to 10, $Y^1$ signifies CN, $N_3$, $COOR^{26}$ and $R^{25}$ and $R^{26}$ independently of each other signify $C_1$-$C_6$ alkyl, in particular methyl, ethyl, n- or isopropyl, or $C_3$-$C_6$ cycloalkyl, in particular cyclopropyl, cyclopentyl or cyclohexyl.

A particularly preferred structure of the structural units B mentioned under 1) has formula (Vb)

$$CH_3\text{---}CH_2\text{---}\underset{\underset{CH_3}{|}}{\overset{\overset{CN}{|}}{C}}\text{---}N=N\text{---}\underset{\underset{CH_3}{|}}{\overset{\overset{CN}{|}}{C}}\text{---}CH_2\text{---}CH_3, \quad \text{(Vb)}$$

i.e. p signifies 2, $R^{25}CH_3$, and $Y^1CN$.

A particularly preferred structure of the structural units B mentioned under 4) conforms to formula (VIII) with l=0 and $R^{24}$=phenylene.

The structures of formulae (V) to (VIII) which constitute the radical-forming part bear 1 (y in formula (I)=0) or 2 (y in formula (I)=2) reactive groups $X^1$ (cf. description of formula (IX)).

In the azo structures of formula (V) the residues $R^{11}$ and $R^2$ bear this (these) group(s). In the structures of formulae (Va), (Vb), (VI) and (VIII) the terminal hydrogen atoms are replaced by this (these) group(s). The dinitriles of formula (VII) bear this (these) group(s) symmetrically round the central bond in $R^{20}$, $R^{21}$ and/or $R^{23}$.

In detail, the following biologically active initiators of formula (I) can be shown by way of example.

Initiator 1:

$$\left[ \underset{\underbrace{\text{Biotin}}_{\text{biologically active section A}}}{\overset{\text{HN}\overset{\overset{O}{||}}{C}\text{NH}}{\underset{S}{\bigg|}}\text{(CH}_2\text{)}_4\text{C}\overset{O}{\underset{||}{-}}\text{O}\text{---CH}_2\text{---CH}_2\text{---NH}\text{---}\underset{\underset{CH_3}{|}}{\overset{\overset{O}{||}}{C}}\text{---}\underset{\underset{CH_3}{|}}{\overset{\overset{CH_3}{|}}{C}}\text{---N=}}_{\text{radical forming section B}} \right]_2$$

Initiator 2:

$$(\text{Biotin-(CH}_2\text{---CH}_2\text{---O)}_9\overset{O}{\underset{||}{C}}\text{---}\underset{\underset{CH_3}{|}}{\overset{\overset{CH_3}{|}}{C}}\text{---N=})_2$$

Initiator 3:

$$(\text{Oligonucleotide-NH}\text{---}\overset{O}{\underset{||}{C}}\text{---CH}_2\text{---CH}_2\text{---}\underset{\underset{CN}{|}}{\overset{\overset{CH_3}{|}}{C}}\text{---N=})_2$$

Initiator 4:

$$\text{Oligonucleotide-NH}\text{---}\overset{O}{\underset{||}{C}}\text{---CH}_2\text{---CH}_2\text{---}\underset{\underset{CN}{|}}{\overset{\overset{CH_3}{|}}{C}}\text{---N=N---}\underset{\underset{CN}{|}}{\overset{\overset{CH_3}{|}}{C}}\text{---CH}_2\text{---CH}_2\text{---}\overset{O}{\underset{||}{C}}\text{---OH}$$

Initiator 5:

$$\left[ \text{Digoxigenin-}\overset{O}{\underset{||}{C}}\text{---CH}_2\text{---CH}_2\text{---}\underset{\underset{CN}{|}}{\overset{\overset{CH_3}{|}}{C}}\text{---N=} \right]_2$$

Initiator 6:

$$\left[ \text{Biotin-CH}_2\text{---CH}_2\text{---NH}\text{---}\overset{O}{\underset{||}{C}}\text{---NH}\text{---}\underset{}{\underset{}{\bigcirc}}\text{---}\overset{O}{\underset{||}{C}}\text{---O} \right]_2$$

Furthermore a process for the production of biologically active radical-chain initiators of general formula (I)

$$A\text{---}L\text{---}B\text{---}[\text{---}L\text{---}A]_y \quad \text{(I)},$$

has been discovered, characterized in that radical-forming compounds of general formula (IX)

$$X^1\text{---}B\text{---}(\text{---}X^1)_y \quad \text{(IX)},$$

wherein

B is defined as above and $X^1$ can be NCO, NCS, COCl, COOH, CO-O-N-hydroxysuccinimide, OH, $NH_2$, SH, Cl, Br or I and y is 0 or 1, preferably 1, are reacted at temperatures between 0° and 40° C. with 1 or 2 equivalents of biologically active substances A in solvents chemically inert towards the groupings named under $X^1$, such as for example chloroaliphatic compounds, ketones, nitriles, sulphoxides, sulphones etc.

In the case of compounds of general formula (IX), $$X^1\text{---}B\text{---}(\text{---}X^1)_y \quad \text{(IX)},$$

in which $X^1$ signifies COCl or $CONHSO_2Cl$ a proton catcher such as for example pyridine or triethylamine is expediently added to the reaction mixture, whereas if X=COOH the reaction is carried out in presence of carbodiimides, for example dicyclohexylcarbodiimide.

Compounds in which $X^1$ signifies NCO and CO—O—N-hydroxysuccinimide are preferably used as the compound of the formula $X^1$—B—$(-X^1)_y$ in the process according to the invention.

The reaction takes place preferably at between 0° and 30° C., especially between 15° and 25° C., and in particular at ca. 20° C. Preferably ethylene chloride, acetone or acetonitrile are used as solvent.

The compounds of formula (IX) are generally known or can be produced by generally known processes (cf. e.g. U.S. Pat. No. 4,155,937).

The linker grouping L is formed by the reaction of $X^1$ from the formula $X^1$—B—$(-X^1)_y$ with the reactive group in the biologically active structural unit A, for example the carboxyl group in biotin or the amino group in the oligonucleotide.

The biologically active radical-chain starter is isolated by methods known per se, for example, after filtering off the (ionic) by-products possibly formed, by evaporation of the solvent in high vacuum, if low-boiling solvents are used, or by precipitation by adding a suitable precipitant, during which the product according to the invention is usually obtained in a pure form. In cases in which the by-products are not volatile or separable from the compounds according to the invention by recrystallization or filtration, the compounds according to the invention are isolated by methods known per se of liquid chromatography, for example column chromatography or preparative HPLC (high pressure liquid chromatography).

The compounds according to the invention are suitable e.g. as initiators for radical polymerizations. When they are used as radical starters, their decomposition products can be incorporated as end groups into the polymers produced. The polymers so modified with end groups (marker polymers) can be selectively reacted e.g. with substrates that are accessible to a biochemical detection reaction.

Linking reactions with biologically active polymers are thereby possible without a cross-linking between the linking reactants or multiple linkages being able to occur. As a rule only one, or at the most two linking groups per polymer are available. Such valuable monofunctional (reactive) polymers can therefore be readily obtained using the compounds according to the invention.

Suitable monomer structural units for the radical polymerization are for example acrylic acid derivatives, vinyl or styryl compounds or mixtures thereof. Their acid, ester, amide or ketone derivatives, for example, can also be used. The monomer structural units can contain reactive or activable groups, which enable covalent bonding for example to a chelating agent (e.g. 1,3-diamino-2-hydroxypropane-N,N,N',N'-tetraacetic acid) and/or dyes (e.g. coumarins, fluoresceins and rhodamines). Such groups can be for example acid halide, imide ester, benzotriazolyl, isocyanato, isothiocyanato, oxirane or diimide groups. Preferred monomer structural units are (meth)acryloyl chloride, (meth)acrylic acid, N-hydroxysuccinimide ester, (meth)acrylic acid, N-hydroxyphthalimide ester, N-(meth)acryloylbenzotriazole, 3- or 4-isothiocyanatophenyl(methyl)acrylate, 2-isocyanatoethyl-(meth)acrylate, isocyanatoisopropenylbenzene, isopropenyl-α,α-dimethylbenzyl isocyanate, vinyloxirane or a combination of (meth)acrylic acid with carbodiimides.

The process according to the invention is explained in more detail by means of the following examples.
Preparation of biologically active initiators of formula (I)

EXAMPLE 1

(corresponding to initiator 1)

3 mmol biotin is stirred under pure nitrogen at room temperature for 18 hours with 1 mmol 2,2'-azobis[2-methyl-N-(2-hydroxyethyl)propionamide] and 3 mmol dicyclohexylcarbodiimide in 20 ml dry dimethylformamide. The precipitate formed is filtered off. 1 ml concentrated aqueous ammonia solution is added to the filtrate. Stirring is carried out for a further 1 hour at room temperature, and the product is again filtered. The filtrate is poured onto crushed ice and the product according to the invention (initiator I) precipitates. According to DC analysis in methanol: chloroform (2:1, $I_2$ detection) and $^1$H-NMR, the dried and washed precipitate yields the pure product according to the invention.

EXAMPLE 2

(corresponding to initiator 6)

1 mmol p,p'-biisocyanatobenzoyl peroxide is reacted with 2 mmol 1-aminoethanol in methylene chloride. The methylene chloride is evaporated and the residue reacted with biotin and dicyclohexylcarbodiimide as described under Example 1.

EXAMPLE 3

10 g of azobisisobutyronitrile (AIBN) as well as 100 g of polyethylene oxide (molecular weight 400) and polyol E 400 are added to 200 ml of methylene chloride. The solution is cooled to 0° C. and HCl gas is introduced (about 46 g of HCl in 3 hours) until saturation is reached. The resulting clear solution is stirred overnight at 0° C. and then poured slowly with stirring onto 200 g ice/100 g water. After stirring for 2 hours the two phases are separated in a separating funnel, the aqueous phase is subsequently extracted 3 times with methylene chloride and the combined phases are extracted by shaking with an aqueous $NaHCO_3$ solution and water. The organic phase is dried over $Na_2SO_4$ and evaporated in a rotary evaporator at room temperature under a high vacuum. The yield is 41.6 g, corresponding to 70.7% of theory. The $^{14}N$ elementary analysis reveals a content of 3.4% nitrogen (theoretical: 3.1%).

EXAMPLE 4

$COCl_2$ was introduced into a solution consisting of 5 g of the product from Example 1 in 50 ml of tetrahydrofuran. 5.5 g of a viscous oil remain after evaporating the solution to dryness.

EXAMPLE 5 biotinylated starter=initiator 2

1 g of $Na_2CO_3$ and 1 g of biotin hydrazide are heated in 15 ml of dimethyl sulphoxide (DMSO) to 75° C. to form a solution. After cooling the solution to 0° C., 2.02 g of the substance from Example 2 are added and the mixture is stirred overnight at room temperature. The precipitate is filtered off and the filtrate is evaporated in a rotary evaporator; the residue is taken up in chloroform, extracted by shaking with a $NaHCO_3$ solution and water and the organic phase is dried over $Na_2SO_4$. After evaporating off the solvent, 1.26 g of a viscous oil remains.

EXAMPLE 6

Preparation of oligonucleotide initiators

To 1.5 mg (0.26 μmol) of the 5'-aminolink-oligonucleotide of the sequence ATCCAGTTGTGTCTTCAAC in sodium phosphate buffer (pH=7.5) there is added a solution of 6 mg (12.6 μmol) of 4,4'-azobis(4-cyanopentanoic acid N-hydroxysuccinimidyl ester) in dimethylformamide. The reaction mixture is stirred for 72 h at room temperature. The reaction product is isolated by means of preparative HPLC (high pressure liquid chromatography) on an RP 18 column with a gradient of acetonitrile in 0.1M triethylammonium acetate increasing linearly over 30 minutes. Yield 35% of theory.
Use

EXAMPLE 7

Preparation of a marker polymer from initiators with biotin as biologically active end group The following are dissolved in 10 ml dry dimethyl sulphoxide:

a) 1.5 g sodium p-styrenesulphonate
b) 0.5 g coumarin dye 1 and c) 100 mg of the initiator from Example 5
Coumarin dye of the formula:

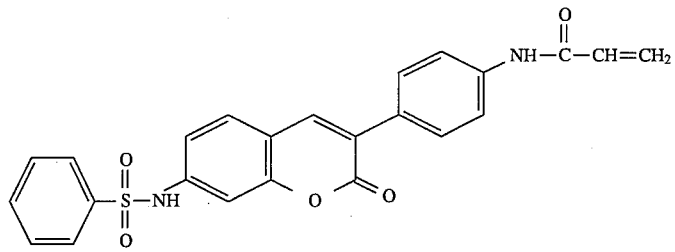

The solution is scavenged thoroughly with pure nitrogen, heated to 70° C. and maintained for 16 h at this temperature. The untreated charge is precipitated in 200 ml methanol, filtered by suction, dried and subjected to an ultrafiltration (rejection limit 10,000 Dalton). The water-soluble, fluorescent polymer has an average molecular-weight of 110,000 Dalton ($M_n$) and can be used directly for reactions with avidin or streptavidin.

EXAMPLE 8

Production of a marker polymer from initiators with oligonucleotide as biologically active end group.

The procedure is just as in Example 7, but the initiator from Example 6 is used instead of the initiator from Example 1, and 1.2 ml of dimethyl sulphoxide is used instead of 10 ml:

a) 0.3 g sodium p-styrenesulphonate b) 0.1 g coumarin dye 1 (for formula, see Example 7)

c) 0.5 mg of the initiator from Example 6.

The polymer has an average molecular weight of 500,000 ($\overline{M}_n$) and can be used directly in the gene probe test for the identification of DNA or RNA of the complementary sequence of the oligonucleotide.

Biologically active substances marked with the marker polymers

EXAMPLE 9

Double marking of the polymer oligonucleotide probe

For detection of the coupling of the oligonucleotide probe to the polymer and for comparison of the sensitivity of detection of the fluorescent dye bound in the polymer with that of the conventional phosphorus$^{32}$ ($P^{32}$) or digoxigenin markings, a double marking of the polymer oligonucleotide probe was carried out. The reactive 5'-amino-oligonucleotide probe with the 19-mer nucleotide sequence 5'd ATC-CAGTTGTGTCTTCAAC from Example 6 was marked with alpha $P^{32}$-dCTP at the 3' end, using an end-group marking kit of the Boehringer Mannheim Company. As an alternative, the end group marking was carried out non-radioactively with digoxigenin-dUTP. In a 50 μl batch with 10 μl reaction buffer (potassium cacodylate 1 mol/l; TRIS/HCl 125 mmol/l; beef serum albumin 1.25 mg/ml; pH 6.6; 25° C.), 1–2 μg oligonucleotide, 5 units terminal transferase, cobalt chloride ($COCl_2$) 2.5 mmol/l and 25 μCi alpha $P^{32}$-dCTP, after 60 minutes at 37° C. ca. 50% end marking is achieved.

The coupling to the polymer was carried out as described in Example 8.

The polymer was precipitated in ethanol and then dissolved in 1 ml twice-distilled water. By gel electrophoresis in 17% polyacrylamide gel it was demonstrated that the oligonucleotide is bound to the polymer.

With the double-marked polymer-oligonucleotide probe, which made evidence possible about the fluorescence of the coumarin fluorescent dye bound in the polymer or about the $P^{32}$ or digoxigenin bound in the oligonucleotide, a slot blot hybridization as described in the following Example 10 and a liquid hybridization as described in Example 11 were carried out.

EXAMPLE 10

Slot blot hybridization with polymer-oligonucleotide probe.

The hybridization was carried out according to conventional methods at an incubation temperature of 40° to 68° C. According to the hybridization temperature, various substances were added.

Dextran sulphate or other polymers were used in order to raise the rate and degree of hybridization. Detergents and blocking reagents such as dried milk, Denhardt's solution, heparin or sodium dodecylsulphate (in the following named SDS) were added to suppress the non-specific binding of the DNA to the membrane. Denaturing agents such as urea or formamide can be used in order to reduce the melting temperature of the hybrids, so that lower hybridization temperatures can be applied.

Furthermore, the non-specific bonding of gene probes to non-homologous DNA on the blot can be reduced by addition of heterologous DNA.

To prepare for the hybridization, 50–500 ng of the unmarked genomic DNA of Nitrosomonas europeae was first denatured for 5 minutes at 100° C., cooled to 0° C. and then applied to pretreated nitrocellulose or nylon membranes with the aid of a Minifold II filtration device of the Schleicher and Schüll Company and fixed for 2 hours at 80° C. The filters were hybridized in a sealed plastic film bag or plastic box with at least 20 ml of hybridization solution per 100 cm$^2$ of filter at 68° C. for at least 1 hour.

The solution was replaced by 2.5 ml/100 cm$^2$ filter of hybridization solution 1 to which 100 ng polymer-oligonucleotide probe from Example was added. The filters were incubated for at least 6 hours at 68° C. with gentle shaking.

The filters were then washed for 2×5 minutes at room temperature with at least 50 ml 2×SSC, 0.1% SDS per 100 cm$^2$ filter and 2×15 minutes at 68° C. with 0.1×SSC, 0.1% SDS. The filters were then used directly for the detection of the hybridized DNA.

Solutions:

20×SSC: 3M NaCl, 0.3M Na citrate pH 7.0

Hybridization solution I:
  5×SSC; 0.1% N-lauroylsarcosine,
  Na salt; 0.02% SDS; 0.5% blocking reagent (Boehringer Mannheim)
Dissolve solution at 50°–70° C.

Other hybridization solutions that likewise can be used for the slot blot hybridization are e.g.:

Hybridization mix 2:
  50% formamide 7×SSC;
  2×Denhardt's solution
  (100×Denhardt's: 2% Ficoll, 2% polyvinylpyrrolidone, 2% beef serum albumin)
  300 gg/ml calfs thymus DNA Hybridization mix 3:
  6×SSC; 10×Denhardt's solution;
  50 µg herring sperm DNA,
  beef serum albumin 0.1%

Hybridization mix 4:
  5×SSC; PEG; 5% dried milk powder
  0.01M sodium pyrophosphate;

Detection was carried out by means of the coumarin fluorescent dye bound in the polymer of the oligonucleotide probe. The fluorescing slot blots of the filter were evaluated quantitatively in a Shimadzu CS930 scanner. Through the double marking of the oligonucleotide with $P^{32}$ by 3' endgroup marking with terminal transferase, an interpretation of the hybridization experiment by means of autoradiography was also possible. To this end the filter was fixed onto a glass plate and an X-ray film then superimposed and exposed for 2–5 hours. After the development of the film the blackening of the slot blot was evaluated quantitatively with a Shimadzu scanner. Alternatively other methods of detection also were used. With digoxigenated polymer-oligonucleotide probes, a dyestuff detection was carried out with alkaline phosphatase conjugated antibodies and bromochloroindolyl phosphate and nitro blue tetrazolium or a chemiluminescence read-out with alkaline phosphatase and AMPPD 3-(2'-spiroadamanntane)-4-methoxy-4-(3"-phosphoryloxy)-phenyl-1,2-dioxetaneassubstrate.

Through the double marking a direct comparison of the sensitivity of various detection systems was possible.

Result

As a result of the signal amplification of the coumarin dye molecules in the polymer (ca. 200 dye molecules/polymer) of the oligonucleotide probe, with the detection of 1–0.1 pg DNA almost the same sensitivity was reached as with enzymatic detection methods. Through the use of a polymer carrier for the coumarin dye molecules a sensitivity higher by a factor 100–1000 than with the conventional marking with fluorescent dyes by way of fluorescent nucleotide structural units is achieved.

EXAMPLE 11

Liquid hybridization with the polymer-oligonucleotide probe

Liquid hybridizations were carried out as sandwich hybridizations with streptavidin-coated magnetic particles of the Dynal Company, Hamburg for separation of the hybridization complex.

The liquid hybridization tests were carried out as sandwich tests with 100 ng 5'-biotinylated capture oligonucleotide probe with the nucleotide sequence 5'dCTGCTCGTAGACAATGCGT, 100 ng polymer oligonucleotide probe as in Example 8 (detector gene probe) and Nitrosomonas target-DNA in various concentrations (50 ng–1000 ng) in a volume of 50 µl.

After 50 minutes' heating at 100° C. followed by cooling at 0° C., 50 µl 2×hybridization mix 1 of Boehringer Mannheim were added and hybridization carried out for 1 hour at 68° C. The magnetic beads were pretreated with 1×hybridization mix 1 and after separation by means of a magnet, the liquid was pipetted off and added to the hybridization charge and incubated at room temperature for ½ hour with gentle movement. The coupled hybridization complex was separated with the beads, the remaining liquid pipetted off and washing carried out, once with buffer A (2×SSC; 0.1% SDS) and then twice with buffer B 0.1 SSC; 0.1% SDS).

Subsequently 500 µl of twice-distilled water were added and the fluorescence of the polymer-oligonucleotide probe in the hybridization complex measured in a fluorescence photometer with 375 nm excitation and 495 nm emission.

In parallel therewith, the blocking reaction and antibody reaction was carried out for detection of the hybridization via chemiluminescence. The beads charged with DNA were treated once with 150 µl wash buffer (0.1M maleic acid, 0.1M NaCl, pH 7.5, 0.3% Tween 20), and after separation and pipetting off of the wash buffer 400 µl buffer 2 (0.1M maleic acid; 0.15M NaCl, pH 7.5; 1% blocking reagent (Boehringer)) added. After ½ hour incubation at room temperature, the mixture was separated, the liquid pipetted off and 100 µl antibody conjugate solution (AK 1:10,000 in buffer 2) added and the mixture incubated for ½ hour at room temperature. The mixture was then separated, liquid pipetted off and treatment carried out with 400 µl wash buffer for 2×15 minutes with gentle movement. The mixture was then separated and treatment carried out with 150 µl buffer 3 (0.1M TRIS/HCl buffer with 0.1M NaCl and 50 mM $MgCl_2$, pH 9.5). The mixture was again separated and incubation carried out with detection solution with AMPPD 1:100 in buffer 3 for 15 minutes at 37° C. on the water bath, and then the chemiluminescence measured in the luminescence photometer at 477 nm (Lumacounter of Lumac).

Result

As a result of the signal amplification of the coumarin dye in the polymer a clearly higher sensitivity was reached than with direct fluorescence marking of the DNA. The sensitivity was higher by a factor 100–1000. The detection limit, at 1–0.1 pg DNA, almost reached the chemiluminescence sensitivity.

EXAMPLE 12

Hybridization of the polymer-oligonucleotide probe with amplified DNA

Through this sensitivity increase, the direct and thereby particularly simple detection by means of the fluorescence of the polymer-oligonucleotide probe becomes a very good alternative by comparison with the known detection techniques such as chemiluminescence, bromochloroindolyl phosphate/nitro blue-tetrazolium dye reaction and the radioactive methods.

The amplification of the target DNA was carried out by the polymerase chain reaction (EP-A 200 362; 201 184) and alternatively by the method of hairpin amplification (EP-A 427 074).

Used for the PCR reaction were 2 µg genomic DNA of Nitrosomonas europae, 2 µmol primer 1 (5'dATCCAGTTGCTTCAAC) and primer 2 (5'ACTGGCAGGCAGCAG), 2.5 units Taq-polymerase of Cetus/Perkin-Elmer as well as in each case 200 µmol dNTPS in a total of 100 µl PCR buffer (50 mM KCl, 10 mM TRIS/HCl pH 8.3), 1.5 mM $MgCl_2$ and 0.01% gelatine. The amplification was carried out in a PCR processor of the Cetus/Perkin-Elmer Company.

With the charges, first an initial melting of the DNA was carried out for 2 minutes 30 seconds at 94° C., then per cycle the DNA was denatured for 1 minute at 94° C., the primer annealing carried out for 2 minutes at 40°–45° C. and the primer extension for 3 minutes at 72° C. Finally, after 35 cycles a 20-minute extension was carried out at 72° C. and the charges cooled at 4° C.

The amplified DNA was denatured for 5 minutes at 100° C. and the charges then immediately cooled to 0° C., 200 µl ice-cold 20×SSC were added and the mixture immediately applied to nitrocellulose or nylon membranes with the aid of a Minifold II filtration device of the Schleicher and Schüll Company. The DNA on the filters was then fixed for 2 hours at 80° C.

The slot blot hybridization with the polymer-oligonucleotide probe and the detection was carried out analogously to Example 11 as described.

Result:

Through the combination of the target nucleic acid amplification with the signal amplification of the coumarin dye in the polymer a sensitivity was reached that made possible the detection of individual DNA molecules. The interpretation via polymer fluorescence becomes thereby a true alternative to the sensitive chemiluminescence method. In contrast to enzymatic chemiluminescence formation, the fluorescence in the polymer can be measured directly.

I claim:

1. Biologically active initiators of the formula (I)

$$A—L—B—[—L—A]_y \quad (I)$$

wherein

A represents a biotin moiety;

B represents a radical forming moiety derived from covalent attachment to the biotin moiety of an azo structure of the general formula (V):

$$R^{11}—N=N—R^{12} \quad (V),$$

wherein $R^{11}$ and $R^{12}$ signify $C_1$–$C_{20}$ alkyl, $C_3$–$C_{10}$ cycloalkyl, $C_7$–$C_{20}$ aralkyl or the group

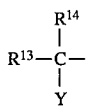

and

Y signifies CN, $N_3$ or

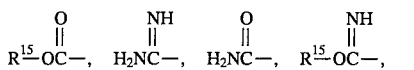

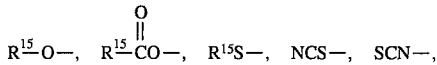

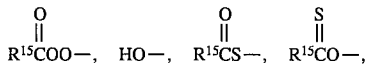

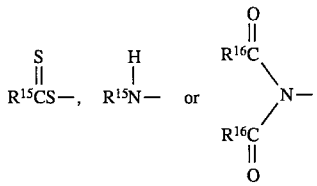

$R^{13}$, $R^{14}$ and $R^{15}$ independently of each other signify $C_1$–$C_{20}$ alkyl or $C_3$–$C_6$ cycloalkyl or, if $R^{13}$ and $R^{14}$ are linked, $C_2$–$C_{30}$ alkylene or additionally one of the groups $R^{13}$ or $R^{14}$, but not both simultaneously, signifies phenyl, tolyl, xylyl, benzyl or phenethyl, $R^{16}$ independently signifies $C_1$–$C_6$ alkyl, $C_3$–$C_6$ cycloalkyl or $C_6$–$C_{12}$ aryl;

and L represents a linker group which links the biotin moiety to $R^{11}$ and $R^{12}$ on the radical forming moiety, said linker being a covalent bond or selected from the group consisting of:

—$SO_2$—, —COO—, —$SO_2$NH—, —CO—NH—, —NH—CO—O—, —NH—CS—O—, —NH—CO—NH—, —NH—CS—NH—, —O—, —NH—, —S— and Y represents the number 0 or 1.

2. Biologically active initiators according to claim 1, wherein

B is an azo structure of formula (Va)

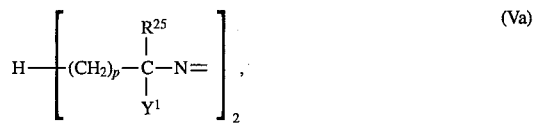

in which p signifies the numbers 1 to 20, $Y^1$ signifies CN, $N_3$, $COOR^{26}$ and $R^{25}$ and $R^{26}$ independently of each other signify $C_1$–$C_6$ alkyl or $C_3$–$C_6$ cycloalkyl.

3. A biologically active initiator as claimed in claim 1, selected from the group consisting of:

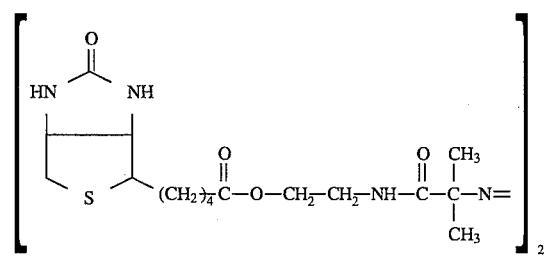

and

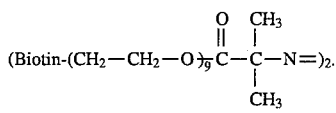

4. A process of preparing a polymeric biological marking reagent which comprises radically polymerizing at least one polymerizable monomer in the presence of the biologically active initiator of claim 1.

* * * * *